(12) United States Patent
Cadet et al.

(10) Patent No.: US 10,449,128 B2
(45) Date of Patent: Oct. 22, 2019

(54) FIBROUS SUPPORT COMPRISING PARTICLES CONTAINING A PARTIALLY WATER-SOLUBLE ACTIVE AGENT, PARTICLES, AND METHODS FOR PRODUCING SAID PARTICLES

(71) Applicant: SATISLOH AG, Baar (CH)

(72) Inventors: Mamonjy Cadet, Charenton-le-Pont (FR); Camille Meridiano, Charenton-le-Pont (FR); Hervé Huilier, Errevet (FR); Adeline Callet, Exincourt (FR)

(73) Assignee: SATISLOH, Baar (CH)

( * ) Notice: Subject to any disclaimer, the term of this patent is extended or adjusted under 35 U.S.C. 154(b) by 0 days.

(21) Appl. No.: 15/327,732

(22) PCT Filed: Jul. 20, 2015

(86) PCT No.: PCT/FR2015/051997
§ 371 (c)(1),
(2) Date: Jan. 20, 2017

(87) PCT Pub. No.: WO2016/012711
PCT Pub. Date: Jan. 28, 2016

(65) Prior Publication Data
US 2017/0202756 A1    Jul. 20, 2017

(30) Foreign Application Priority Data
Jul. 21, 2014  (FR) ...................................... 14 57030

(51) Int. Cl.
| | | |
|---|---|---|
| *D06M 23/12* | (2006.01) | |
| *B01J 13/12* | (2006.01) | |
| *B01J 13/18* | (2006.01) | |
| *B01J 13/22* | (2006.01) | |
| *C11D 1/00* | (2006.01) | |
| *C11D 1/88* | (2006.01) | |
| *C11D 17/04* | (2006.01) | |
| *A61K 8/11* | (2006.01) | |
| *C11D 17/00* | (2006.01) | |
| *A01N 25/28* | (2006.01) | |
| *B01J 13/08* | (2006.01) | |
| *A61Q 19/00* | (2006.01) | |
| *A61K 8/02* | (2006.01) | |
| *A01N 25/08* | (2006.01) | |
| *A61K 8/42* | (2006.01) | |
| *A61Q 17/00* | (2006.01) | |
| *A61Q 17/02* | (2006.01) | |
| *B01J 13/04* | (2006.01) | |
| *C11D 11/00* | (2006.01) | |

(52) U.S. Cl.
CPC ................ *A61K 8/11* (2013.01); *A01N 25/08* (2013.01); *A01N 25/28* (2013.01); *A61K 8/0208* (2013.01); *A61K 8/42* (2013.01); *A61Q 17/005* (2013.01); *A61Q 17/02* (2013.01); *A61Q 19/00* (2013.01); *B01J 13/043* (2013.01); *B01J 13/08* (2013.01); *B01J 13/18* (2013.01); *B01J 13/22* (2013.01); *C11D 11/0035* (2013.01); *C11D 17/0039* (2013.01); *C11D 17/049* (2013.01); *D06M 23/12* (2013.01); *A61K 2800/412* (2013.01); *A61K 2800/413* (2013.01); *A61K 2800/624* (2013.01)

(58) Field of Classification Search
None
See application file for complete search history.

(56) References Cited

U.S. PATENT DOCUMENTS

| | | | | |
|---|---|---|---|---|
| 5,997,261 | A | 12/1999 | Kershaw et al. | |
| 6,979,478 | B1* | 12/2005 | DeNuccio | B05D 5/06 427/162 |
| 2002/0055560 | A1* | 5/2002 | Nanbu | B01J 13/16 524/21 |
| 2006/0128831 | A1* | 6/2006 | Cook | C09J 133/04 523/160 |
| 2010/0320421 | A1* | 12/2010 | Calle | B01J 13/14 252/388 |

FOREIGN PATENT DOCUMENTS

| | | |
|---|---|---|
| EP | 0407257 | 1/1991 |
| EP | 1418211 | 5/2004 |
| EP | 1533415 | 5/2005 |
| EP | 2080552 | 7/2009 |
| FR | 2868684 | 10/2005 |
| FR | 2995222 | 3/2014 |
| GB | 1242689 | 8/1971 |
| JP | H02300387 | 12/1990 |
| JP | 2005296920 | 10/2005 |
| JP | 2009195648 | 9/2009 |
| WO | WO2011/080472 | 7/2011 |
| WO | WO2012038666 | 3/2012 |
| WO | WO2013013929 | 1/2013 |

OTHER PUBLICATIONS

Croda, "Span and Tween," 2009, pp. 1-6.*

* cited by examiner

*Primary Examiner* — Brian Gulledge
(74) *Attorney, Agent, or Firm* — Norton Rose Fulbright US LLP

(57) ABSTRACT

The invention relates to a support consisting of natural and/or synthetic fibers which particles are held, which are preferably water-soluble, comprising at least one active agent, said particles at least partially releasing the active agent(s) under the effect of an external stress, characterized in the active agent has a water-solubility of between 0.1 and 60 wt. %, preferably between 0.1 and 30 wt. %.

4 Claims, 3 Drawing Sheets

SEM photograph of the acacia/Ethyl butylacetylaminopropionate (75/25) microcapsules Optical photograph at 400x and 1000x of the acacia/Ethyl butylacetylaminopropionate microcapsules SEM photograph of the acacia/xylitol microcapsules

*Optical photograph at 400x*

SEM, photograph x2000

Optical microscopy observation x 400

Particle size distribution of the particles obtained d(0.5)=40μm

Observation with the optical microscope x400

Optical microscopy carried out on the wipes before and after treatment

Optical microscope (x1000)

FIBROUS SUPPORT COMPRISING PARTICLES CONTAINING A PARTIALLY WATER-SOLUBLE ACTIVE AGENT, PARTICLES, AND METHODS FOR PRODUCING SAID PARTICLES

CROSS-REFERENCE TO RELATED APPLICATIONS

This application is a national phase application under 35 U.S.C. § 371 of International Application No. PCT/FR2015/051997 filed 20 Jul. 2015, which claims priority to French Patent Application No. 1457030 filed 21 Jul. 2014. The entire contents of each of the above-referenced disclosures is specifically incorporated herein by reference without disclaimer.

The present invention relates generally to supports made of natural and/or synthetic fibers, preferably flexible fibers, in which are retained particles comprising, within them, at least one active agent which is partially soluble in water, the particles releasing, at least in part, the active agent(s) under the effect of an external stress, and also to the process for the manufacture of such supports.

The invention also relates to particles comprising at least one active agent which is partially soluble in water and to their processes of manufacture.

Functional textiles capable of delivering, to a surface, an active agent retained by the textile are known. The active agent can be of varied nature, for example a detergent, antifogging, bactericidal or biocidal agent, a dermatological therapeutic or cosmetic active principle (moisturizing, emollient, cleaning, relipidizing, lipolytic, exfoliant, tightening, pigmenting or depigmenting, antiseptic, disinfecting or healing) or a scenting and odorizing agent.

The surface to which the active agent is delivered can be of any nature, for example the skin, a mineral or organic glass, a metal or an alloy, or the like.

A more particular field of the invention is that of functional textiles used in optics, in particular in ophthalmic optics, for cleaning the surfaces of the optical article or for conferring [or re-establishing] specific properties thereon, in particular for conferring or re-establishing antifogging properties at these surfaces.

Known antifogging fabrics, also known as antifogging wipes, are obtained by impregnation of the liquid active agent into the fabrics.

Antifogging wipes of this type are described, inter alia, in the patent FR 2 868 684 and the patent application JP 2009/195648 and the patent application WO2013013929. In this case, the active agent is not protected and thus can be degraded as a result of physical or chemical interactions with the external environment (erosion, radiation, moisture, and the like). Washing these wipes would remove the antifogging agent present (in particular if the agent is partially soluble in water) and would destroy the function of antifogging recharging with the wipe. The durability of these wipes is thus limited by their absence of resistance to washing.

It has been proposed to immobilize the antifogging agent on the textile within microcapsules. In this way, the antifogging agent is then released toward the surface to 27891365.1 be treated by rupture of the membrane of the microcapsule or by erosion of the microsphere during the exercise of a pressure of the textile on the glass. The antifogging agent is thus delivered in a controlled way during the use of the textile and is not leached by possible washing or copious contact with water.

Thus, the Japanese patent JP 02300387 describes a microfiber textile in which microcapsules containing an antifogging agent are immobilized. The encapsulating agent is polyurethane or a urea-formaldehyde resin. The antifogging agent is a fluorine-based surfactant. There is no indication that the surface-active agent is partially soluble in water. The patent JP 2005 296920 describes a textile coated with antifogging agent having an improved durability with regard to wear and washing. Numerous surfactants are cited as antifogging agents. The textile is an acrylic textile and the capsules are made of porous silica, gelatin, polyurea, urea-melamine resins.

The patent EP 2 080 552 describes a process for the encapsulation in a polysiloxane membrane of an either hydrophilic or hydrophobic compound. No mention is made of active agents having a partial solubility in water.

The patent application WO 2012 038666 also describes the manufacture of polysiloxane microcapsules which can be functionalized in order to be grafted to textile fibers having hydroxyl functional groups. Here again, the active agent is either hydrophilic or hydrophobic. Mention is never made of a partially water-soluble active agent.

The patent FR 2 995 222 describes a process of microencapsulation by drop "congealing". The active agent is either liposoluble or lipodispersible or water-insoluble. An active agent which is partially water-soluble is never envisaged.

The patent EP 1 533 415 describes melamine-formaldehyde microcapsules containing a liposoluble, lipodispersible or water-insoluble active principle.

The known encapsulation technologies conventionally used in the textile industry do not make it possible to encapsulate active agents which are partially soluble in water, such as surfactants, in particular fluorinated surfactants, comprising a hydrophilic chain (for example polyethylene), or such as ethyl 3-[acetyl(butyl)amino]propanoate (IR 3535 biocide, also used as insect repellent) or such as caffeine.

More generally, conventional encapsulation technologies involve the preparation of oil-in-water or water-in-oil emulsions, which require the addition of (amphiphilic) surfactants for the control of the emulsion. The encapsulation of active products which are partially soluble in water (which can also be amphiphilic) means that these molecules are then re-encountered distributed between the two phases of the emulsion. In point of fact, the aqueous phase (which is generally the dispersing phase of the emulsion) is the site of chemical reactions, very sensitive to the conditions of the medium (pH, ionic strength, concentration), resulting in the formation of the encapsulation membranes. The presence of measurable amounts of the active agent in this phase of thus harmful to the formation of the capsules.

The advantage of the encapsulation of the active agent (for example an antifogging agent) is to protect it with respect to the environment (radiation, humidity, chemical reactivity) and also to control its release over the surface by pressure or by rubbing or by simple contact (for example during the wiping of spectacle lenses, application of the textile to the skin or a substrate).

In addition, it is important for the active agents to be mainly located at the core of the particles and not at their peripheries for prolonged use of the wipes.

A first object of the present invention is to provide a support consisting of fibers for active principles which is an alternative to those existing in the prior art.

Another object of the present invention is to provide a support which consists of fibers on which are retained particles containing, within them, at least one active agent which is partially soluble in water and overcoming the disadvantages of the prior art.

Another object of the invention is a process for the manufacture of such a support, and also processes for the manufacture of particles comprising, within them, at least one active agent which is partially soluble in water.

The above aims are achieved according to the invention by the preparation of a support made of natural and/or synthetic fibers, preferably a flexible support, in which are retained particles, preferably water-insoluble particles, comprising, within them, at least one active agent having a partial solubility in water of 0.1 to 60%, preferably of 0.1 to 30%, by weight, said particles releasing, at least in part, the active agent(s) under the effect of an external stress.

Definitions and Description of the Elements of the Invention

Particle: object of any shape (preferably spherical or quasi-spherical) with a size of 100 nm to 200 µm, preferably of 100 nm to 100 µm and better still of 100 nm to 50 µm, and containing at least one active agent. Preferably, the particles are insoluble in water. The release, at least in part, of the active agent takes place under the action of an external stress, for example a mechanical, thermal or chemical stress.

Microcapsule: Particle of any shape (for example, spherical or quasi-spherical) with a size of 100 nm to 200 µm, defined by a casing or a membrane for example made of polymer material of the type of aminoplast, urea-formaldehyde resin, phenolic resin, fatty acids, fatty acid esters, waxes of vegetable origin, polysiloxanes, organosiloxanes, cellulose derivatives, gums of vegetable origin which are optionally modified, including a liquid or solid phase in which the active agent is present, either in the pure state or dissolved or dispersed within a host phase in proportions preferably of 0.01 to 99.999% by weight. The content/container ratio by weight can vary from 80/20 to 1/999. The release of at least a portion of the active agent takes place by degradation of the membrane, either under a mechanical stress or under a thermal stress.

Microsphere: Particle of any shape (for example, spherical or quasi-spherical) with a size of 100 nm to 200 µm, consisting of at least one vector known as matrix, for example of the type of fatty acids, fatty acid esters, waxes of vegetable origin, polysiloxanes, organosiloxanes, cellulose derivatives, gums of vegetable origin which are optionally modified, and of at least one active agent dissolved or dispersed within the matrix in which the active agent is present either in the pure state or dissolved or dispersed in a host phase in proportions of 0.001 to 99.999% by weight. The content/matrix ratio by weight can vary from 60/40 to 1/999. The matrix is insoluble in water and is solid at ambient temperature (20° C.) and preferably up to 30° C., indeed even 35° C. It is also either solid or insoluble in water at the temperatures of manufacture of the liberating textiles.

The release of at least a portion of the active agent can be carried out by application of a thermal stress (for example, application of a temperature greater than the melting point or the softening point or the glass transition temperature of the matrix, according to the nature of the matrix). The release can also be carried out under a mechanical stress, for example by rubbing, by erosion or by creep. The release of the active agent can also take place under a chemical stress, for example application of solvent or modification of the pH.

Support

The supports are all materials made of fibers, preferably flexible fibers. These supports are generally nonwoven textiles or papers, textiles manufactured by weaving or by knitting, felts and cellulose wads.

The fibers can be natural or synthetic fibers, such as cotton, flax, hemp, jute, silk, wool, cellulose, polyamide, acetate, viscose, modal, acrylic or polyester fibers and chlorofibers.

The supports preferred according to the invention for ophthalmic and/or antifogging applications are woven or knitted, preferably knitted, fabrics made of microfibers.

As is known, a woven material is obtained by perpendicularly intertwining two sets of yarns in the longitudinal (warp) direction and in the cross (weft) direction, whereas a nonwoven material is a manufactured sheet consisting of webs or laps of oriented or non-oriented fibers, bonded by friction, cohesion and/or adhesion.

A knitted fabric is obtained by looping one or more yarns in order to form stitches which are interlaced with one another.

According to the invention, use is preferably made, for ophthalmic and/or antifogging applications, of a knitted fabric with a number of stitches/cm$^2$ of at least 300, preferably at least 400, better still at least 500 and even better still greater than 700. The optimum range for the number of stitches/cm$^2$ is greater than 800 and even better still greater than 900 stitches/cm$^2$. If necessary, a person skilled in the art will refer to the standard NF EN 14971 relating to this feature of the invention.

The fabric used in the invention preferably comprises at least 80% by weight of microfibers, better still at least 90% by weight of microfibers, preferably at least 95% by weight and better still 100% by weight of microfibers. "Microfibers" is understood to mean textile fibers, the linear density of which is less than 1.3 decitex (1.3 g/10 km). The preferred microfibers have a linear density of less than 1 decitex.

The fabric made of microfibers comprises, according to the invention, hydrophilic polymer microfibers and lipophilic polymer microfibers.

The hydrophilic polymer microfibers exhibit an affinity for water, whereas the lipophilic polymer microfibers exhibit an affinity for oils.

The lipophilic polymer exhibits affinities with sebum-type soiling, whereas the hydrophilic polymer exhibits an affinity with respect to the moisture present at the surface of the substrate treated by the wipe, preferably an ophthalmic lens.

A hydrophilic polymer preferably used is a polymer capable of a degree of water uptake of greater than or equal to 2%, better still of greater than or equal to 3%.

The degree of water uptake is the ratio of the conditioned weight of a sample (after 24 hours at 20° C. and a degree of ambient humidity of 65%) to the anhydrous weight obtained in an oven at 105° C.±2° C. (drying until a constant weight is obtained).

The water uptake measurement is known to a person skilled in the art who can refer, if necessary, to the standard EN ISO6741.

It is preferable for the degree of water uptake of the hydrophilic polymer to be less than 10%, better still less than 8% and even better still less than or equal to 7%.

A lipophilic polymer preferably used exhibits a degree of water uptake of less than 2%, better still of less than 1.5% and even better still of less than 1%.

The preferred hydrophilic polymers are polyamides 6,6 (degree of water uptake (DWU) of from 2.5% to 6%), polyamides 6 (DWU of 5.75%) and celluloses (DWU of from 8% to 13%).

The preferred lipophilic polymers are polyesters (DWU of from 0.15% to 0.50%) and polypropylenes (DWU of from 0.05% to 0.50%).

The fabric made of microfibers preferably comprises polyamide microfibers and polyester microfibers, better still from 60% to 85% by weight of polyester microfibers and from 15% to 40% by weight of polyamide microfibers. An example of such a fabric is the Cémoi™ fabric, composed of 69.5% by weight of polyester microfibers and of 30.5% by weight of polyamide microfibers. A fabric composed of 79% by weight of polyester microfibers and of 21% by weight of polyamide microfibers, supplied by Kelnet, is also suitable.

Preferably, the fabric made of microfibers predominantly comprises microfibers of triangular cross section. Preferably, at least 80% by number of the lipophilic polymer microfibers have a triangular cross section.

The microfibers used can be obtained by splitting fibers, preferably having an "orange segment" structure, the orange segments preferably consisting of lipophilic polymer. Thus, according to a preferred embodiment, the microfibers are obtained from hydrophilic and lipophilic polymer fibers of composite structure, by splitting said composite structure, after weaving or knitting.

For dermatological applications, it is preferable to use textiles having the same compositions as those of the microfibers but having dimensions greater than those of microfibers.

Maintenance of the Particles on the Support

The particles are retained within the support either by immobilization or by attachment.

Immobilization: the particles are deposited on the support without wishing to attach by a covalent bond or via a binder between the particles and the support. This immobilization can be carried out by conventional impregnation techniques with a padding machine, with a lick-roll applicator, by spraying, by dipping, and the like.

Attachment: the particles are conventionally deposited on the support and are attached to the support by an appropriate treatment (thermal crosslinking, light or photon irradiation) of a binder or of a bridging agent in order to form covalent bonds between the support and particles. This attachment improves the resistance to leaching of the supports according to the invention.

Active agent: The active agent is a compound or mixture of compounds which confers one or more given properties on a substrate when it is applied to this substrate.

According to the present invention, the active agent exhibits a partial solubility in water ranging from 0.1% to 60% by weight, preferably from 0.1% to 30% by weight, more preferably from 0.2% to 60%, better still from 0.2% to 40% and even better still from 0.2% to 30% by weight, at a temperature T chosen within the range extending from 20° C. to 95° C., at a pressure of one atmosphere.

Another preferred range of solubility in water is from 0.5% to 60%, preferably from 1% to 60%, better still from 2% to 60% and even better still from 2% to 30% by weight, at a temperature T chosen within the range extending from 20° C. to 95° C., at a pressure of one atmosphere.

Preferably, the solubility is measured at a temperature T of 20° C.

For the solid compounds, the solubility is defined as the percentage by weight of the compound in a solution at equilibrium with the solid phase at the above temperature T and a pressure of one atmosphere. For the liquid compounds (or solids in the pure state), the aqueous mixtures of which separate into two or more phases, the solubility taken into account is the percentage by weight of the specified compound in the water-rich liquid phase at equilibrium at the operating temperature (temperature at which said particles are manufactured (as the case may be, between 20 and 95° C.)) and a pressure of one atmosphere. In particular, the active agent can be an amphiphilic compound, especially a nonionic amphiphilic fluorinated molecule.

The active agent can be an ionic or nonionic, organic or organometallic and surface-active or non-surface-active compound.

The active agent can have varied applicative properties, such as: antifogging, bactericidal, biocidal, detergent, insect repellent, therapeutic, in particular dermatological, or cosmetic.

The active agents having cosmetic properties can be moisturizers, emollients, cleaning agents, relipidizing agents, lipolytic agents, exfoliants, tightening agents, pigmenting or depigmenting agents, fragrances and odorizing agents.

The active agents can also be antiseptics, disinfectants and healing agents.

A category of active agents particularly targeted by the present invention comprises antifogging agents.

The preferred antifogging agents are ionic, nonionic and amphoteric, preferably nonionic, surfactants.

A great variety of surfactants can be employed. These can be ionic (cationic, anionic or amphoteric) or nonionic, preferably nonionic or anionic. However, a mixture of surfactants belonging to these different categories can be envisaged. These surface-active agents are for the most part commercially available.

Preferably, use is made of a surface-active agent comprising poly(oxyalkylene) groups.

Mention may be made, as examples of nonionic surfactants which can be used in the present invention, of poly (alkylenoxy) alkyl ethers, in particular poly(ethylenoxy) alkyl ethers, for example sold by Croda under the Brij® names, alkyl poly(alkylenoxy) amines, alkyl poly(alkylenoxy) amides, polyethoxylated, polypropoxylated or polyglycerolated fatty alcohols, polyethoxylated, polypropoxylated or polyglycerolated fatty α-diols, polyethoxylated, polypropoxylated or polyglycerolated fatty alkylphenols and polyethoxylated, polypropoxylated or polyglycerolated fatty acids, all having a fatty chain comprising, for example, from 6 to 20 and preferably from 8 to 18 carbon atoms, it being possible for the number of ethylene oxide or propylene oxide groups to range in particular from 2 to 100, preferably from 2 to 50, and it being possible for the number of glycerol groups to range in particular from 2 to 30, ethoxylated acetylenic diols, compounds of the block copolymer type comprising both hydrophilic blocks and hydrophobic blocks (for example polyoxyethylene and polyoxypropylene blocks respectively), poly(oxyethylene)-poly(dimethylsiloxane) copolymers and surfactants incorporating a sorbitan group.

Preferred anionic surfactants are those comprising a sulfonic acid group. Mention may be made of alkyl sulfosuccinates, alkyl ether sulfosuccinates, alkyl amide sulfosuccinates, alkyl sulfosuccinamates, the dibasic salts of alkyl polyoxyethylene sulfosuccinic acid, the dibasic salts of alkyl sulfosuccinic acid, alkyl sulfoacetates, the salts of hemiesters of sulfosuccinic acid, alkyl sulfates and aryl sulfates, such as sodium dodecylbenzenesulfonate and sodium dodecyl sulfate, ethoxylated fatty alcohol sulfates, alkyl ether sulfates, alkylamido ether sulfates, alkylaryl polyether sulfates, alkylsulfonates, alkyl phosphates, alkyl ether phosphates, alkylamidesulfonates, alkylarylsulfonates, α-olefinsulfonates, secondary alcohol ethoxysulfates, polyoxyalkylenated ether carboxylic acids, monoglyceride sulfates, polyoxyethylene alkyl ether salts of sulfuric acid, salts of esters of sulfuric acid, N-acyltaurates, such as N-acylmethyltaurine salts, salts of hydroxyalkanemonosulfonic acids or alkenemonosulfonates, the alkyl or acyl radical of all these compounds preferably comprising from 12 to 20 carbon atoms and the optional oxyalkylene group of these compounds preferably comprising from 2 to 50 monomer units. These anionic surfactants and many others which can be used in the present patent application are described in the application EP 1 418 211 and the U.S. Pat. No. 5,997,621.

Mention may be made, as cationic surface-active agents which can be used in the present invention, of salts of primary, secondary or tertiary fatty amines which are optionally polyoxyalkylenated, quaternary ammonium salts, such as tetraalkylammonium, alkylamidoalkyltrialkylammonium, trialkylbenzylammonium, trialkylhydroxyalkylammonium or alkylpyridinium chlorides or bromides, imidazoline derivatives or amine oxides having a cationic nature.

According to one embodiment, the surfactant used comprises a fluorinated surfactant, preferably an amphiphilic fluorinated surfactant. In the case of a fluorinated surfactant, use is preferably made of those comprising at least one fluoroalkyl or polyfluoroalkyl group and better still of those comprising at least one perfluoroalkyl group.

It is possible, in place of a surfactant solution, to use hydrophilic compounds, more particularly compounds devoid of surfactant properties comprising at least one hydrophilic group, preferably a poly(oxyalkylene) group.

The antifogging coating of the invention preferably exhibits a static contact angle with water of less than or equal to 10° and better still of less than or equal to 5°, when it is applied to the substrate for which it is intended.

The preferred agents for antifogging applications are described below.

Polyethylene glycol alkyl monoethers (A) represent a first category of preferred surfactants. They are preferably non-fluorinated. Use will preferably be made, among these, of those of formula:

$$H(OCH_2CH_2)_nOR^1 \quad (I)$$

in which $R^1$ is a linear or branched alkyl group which is optionally substituted by one or more functional groups and which can additionally comprise one or more double bonds, and n is an integer from 1 to 25, preferably from 2 to 20, better still from 2 to 15, even better still from 4 to 15 and ideally from 8 to 12. n can in particular take the values 2, 4, 5, 10 or 20. According to a specific embodiment, n is greater than 6. According to another specific embodiment, n is less than 20 and better still less than 15.

$R^1$ is preferably a linear alkyl group preferably comprising from 10 to 20 carbon atoms, better still a saturated linear alkyl group. Nonlimiting examples of $R^1$ groups which can be used are the dodecyl ($C_{12}H_{25}$), cetyl ($C_{16}H_{33}$), stearyl ($C_{18}H_{37}$) and oleyl ($C_{18}H_{35}$) groups. According to a specific embodiment, the $R^1$ group has 12 or less carbon atoms.

The surfactants of formula (I) preferably have a molar mass of from 180 to 1500 g/mol, better still from 300 to 1000 g/mol and even better still from 350 to 800 g/mol.

Compounds of formula (I) which can be used in the present invention are sold by Croda under the Brij® brand, for example the Brij® products carrying the following numbers: C10, L4, C20 and S10. Among them, Brij® C10 (HLB=12-13) is preferred (compound of formula II with n=10 and $R^1$=n-$C_6H_{13}$).

The surfactants having a sorbitan ring (B) represent a second category of preferred surfactants. Among these, use will preferably be made of those for which the sorbitan ring has n of its four hydroxyl groups functionalized with identical or different OH-terminated polyoxyalkylene groups (preferably polyoxyethylene groups) and p of its four hydroxyl groups functionalized with identical or different $R^1$ groups of formula:

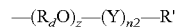

in which $R_d$ is a linear or branched alkylene group, z is an integer ≥1, Y is a divalent group, n2 represents 0 or 1 (preferably, n2=1) and R' is a saturated hydrocarbon group having from 12 to 19, preferably from 13 to 19, carbon atoms, n and p being integers such as n=2 or 3 and p=1 or 2, with n+p=4. Preferably, n=3 and/or p=1.

$R_d$ preferably represents a $C_2$-$C_6$ alkylene group, such as the propylene or ethylene groups, ideally the ethylene group.

The integer z preferably varies from 1 to 40, better still from 2 to 20 and even better still from 2 to 10.

The OH-terminated polyoxyalkylene groups of these compounds preferably comprise from 1 to 40 oxyalkylene groups, better still from 2 to 20 and even better still from 2 to 10 oxyalkylene groups.

The total number of oxyalkylene groups present in the structure of the surfactants (B) preferably varies from 4 to 40, better still from 8 to 30, even better still from 15 to 25 and is ideally equal to 20.

R' is a saturated hydrocarbon group preferably having from 14 to 18 carbon atoms, better still from 15 to 17 carbon atoms. R' is preferably a linear alkyl group. R' is preferably an n-$C_{15}H_{31}$ or n-$C_{17}H_{35}$ group.

Nonlimiting examples of Y groups are alkylene, cycloalkylene, arylene, carbonyl or amido groups, or combinations of these groups, which are linear or branched and optionally substituted. Y is preferably a carbonyl group.

The —$(Y)_{n2}$—R' group is preferably a palmityl group or a stearyl group.

The surfactants (B) are preferably nonionic and are preferably polyoxyalkylene sorbitan fatty acid esters, that is to say polyoxyalkylenated sorbitans esterified once or twice by a fatty acid (Y=carbonyl and n2=1), preferably only once. Better still, the surfactants (B) are polyoxyethylene sorbitan fatty acid esters (Y=carbonyl, n2=1 and R=$CH_2CH_2$), in other words polysorbates with specific chain lengths for the ester group.

A preferred class of surfactants (B) comprises the compounds of formula (II):

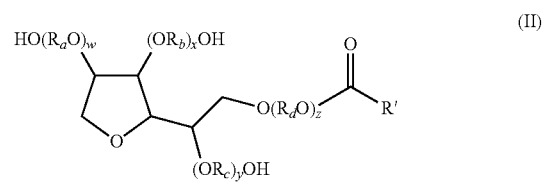

in which $R_a$, $R_b$, $R_c$ and $R_d$ independently represent linear or branched, preferably linear, alkylene groups, preferably $C_2$-$C_6$ alkylene groups, such as the propylene or ethylene groups, w, x, y and z independently represent integers ≥1, preferably ranging from 1 to 40, better still from 2 to 20 and even better still from 2 to 10, and R' is as defined above.

Preferably, w+x+y+z varies from 4 to 40, better still from 8 to 30 and even better still from 15 to 25. Ideally, w+x+y+z=20.

Among the surfactants (B) of formula (II), use will preferably be made of the polyethoxylated compounds of formula (II):

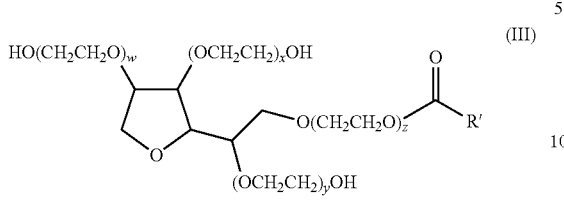

(III)

in which w, x, y, z and R' are as defined above.

The surfactants (B) can be easily synthesized or are commercially available. In particular, the surfactants (B) of formula (II) or (III) are sold under the Alkest™, Canarcel™ or Tween™ brands.

The preferred surfactants (B) are Tween™ 40 (HLB=15.6), also known under the name of polyoxyethylene (20) sorbitan monopalmitate (compound of formula X in which $R'=C_{15}H_{31}$ and w+x+y+z=20), Tween™ 60, also known under the name of polyoxyethylene (20) sorbitan monostearate (compound of formula (III) in which $R'=C_{17}H_{35}$ and w+x+y+z=20), Tween™ 20 and Tween™ 80.

Other surfactants which can be used are the triblock copolymers comprising two ethylene oxide (EO) blocks and one propylene oxide (PO) central block, referred to as "poloxamers", sold in particular by BASF under the name Pluronic® and denoted by $(EO)_x$-$(PO)_y$-$(EO)_z$ or $HO(CH_2CH_2O)_x$—$(CH_2CH(CH_3)O)_y$—$(CH_2CH_2O)_zH$, for example the Pluronic® P-123, L-121, P-65 and P-64 products.

Other surfactants which can be used according to the invention are the polyethoxylated surfactants of fluoroalkyl nature, preferably of formula $F(CF_2)_y$—$(CH_2$—$CH_2O)_{x+1}H$ (IV), in which x and y are integers such that x varies from 1 to 16 and y is less than or equal to 10.

Among these fluorinated surfactants, use may in particular be made of Capstone® FS 3100, Capstone® FS30, Capstone® FS 31, Capstone® FS 34, Masurf FS 1700, Masurf FS 1800, Masurf 2800, Masurf 2900, Zonyl® FSO 100 and Zonyl® FSN 100.

Capstone® FS 3100 is a surfactant comprising a mixture of compounds having variable polyethoxylated chain lengths corresponding to the general formula $F(CF_2)_y$—$(CH_2$—$CH_2O)_{x+1}H$ (IV), more than 90% by weight of which corresponds to the fraction y=6, x being an integer varying from 1 to 14. Capstone® FS3100 contains contents, undetectable by HPLC, of compound of formula (IV) in which y is greater than 6. It is biodegradable.

Zonyl® FSO 100 (HLB=9.1), sold by DuPont, which is a mixture of compounds of formula $F(CF_2)_y$—$(CH_2$—$CH_2O)_{x+1}H$ (IV) in which y takes the values 6, 8 and 10 in respective proportions by weight of the order of 65%, 30% and 5% and x is an integer varying from 2 to 13.

According to one embodiment, the surfactant contains at least one Si—O siloxane unit and also exhibits a surface tension of less than 40 mN/m and better still of less than 35 mN/m. An example of such a surfactant is the compound Coatosil 77 sold by Momentive (formerly Silwet 77, exhibiting a surface tension of 20.5 mN/m), the formula of which is as follows, n being equal to 7.5:

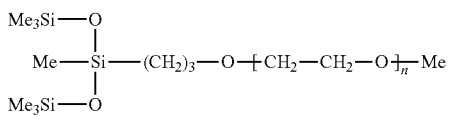

The surface tension of the surfactant, expressed in mN/m, is obtained according to the Wilhelmy plate method: the surface tension is measured for a 0.1% by weight solution (solvent: water). A vertical plate is pulled out of the liquid while measuring the force exerted. The value of the pull force of the plate is noted just before the meniscus detaches. The force thus obtained is divided by the width of the plate, and the value of the surface tension is obtained. The contact angle (0°) between the liquid and the surface of the plate must be guaranteed by intensive cleaning, for example by calcination of the measurement body.

The surfactants envisaged above can be used alone or as a mixture with one or more other surfactants, provided that the characteristics of the mixture in question remain compatible with the properties required according to the invention. Preferably, the surfactants having a hydrophilic-lipophilic balance <5 represent less than 10% of the weight of surfactants, better still less than 5% and even better still 0%. Preferably, the surfactants having a hydrophilic-lipophilic balance >18 represent less than 10% of the weight of surfactants, better still less than 5% and even better still 0%.

Examples of preferred surfactants are those having a hydrophilic-lipophilic balance (HLB)≥5.

Another specific category of active agents comprises antimicrobial compositions. Antimicrobial composition is understood to mean a composition having an activity against bacteria and/or fungi and/or yeasts and/or molds. Mention may be made of biocidal, bacteriostatic, bactericidal, antiyeast, antifungal, fungicidal, fungistatic and/or repellent agents. Particular antimicrobial compositions comprise the specific combination of a nonionic surfactant comprising a hydrophilic unit and a hydrophobic unit, the hydrophilic unit containing poly(oxyalkylene) units of formula $[$—R1-O—Z—$)]_n$, where R1 represents linear or branched alkylene groups, such as propylene or ethylene, and z is an integer equal to or greater than 1, preferably ranging from 1 to 40, the number n of these poly(alkylene) units being equal to or greater than 3, and at least one alcohol with a low molar mass equal to 500 g/mol or less, the nonionic surfactant/alcohol ratio R being such that 2.5≤R≤20, and preferably the content by weight of alcohol, with respect to the total weight of the composition, is from 0.01 to 5%, preferably from 0.01 to 20%. The surfactants are the same as those described above, in particular surfactants of formulae (I), (II), (III) and (IV).

Mention may be made, among the other active agents which can be used in the invention, of:
certain amino acids, such as L-tryptophan, L-lysine, L-arginine or L-alanine;
sugars, such as D-mannitol or xylitol (xylitol has a solubility in water of 39%);
water-soluble vitamins, such as vitamin C (ascorbic acid);
compounds such as codeine, caffeine, 5-fluorouracil (anti-cancer agent) or ethyl butylacetylaminopropionate (IR3535).

Substrates

The substrates, the surfaces of which are capable of being treated with the supports according to the invention, are of varied nature and are, for example, organic or mineral glasses, human or animal skin, human or animal superficial body growths, metals and alloys, plastics, leathers, and the like.

A particular category of substrates are organic or mineral glasses, in particular optical articles, such as ophthalmic lenses, for example spectacle lenses, the surface to be treated of which can optionally comprise functional coatings, such as impact-resistant, scratch-resistant, antireflective, dirt-repelling or photochromic coatings, and the like.

A particular substrate is an optical article (optical lens, for example spectacle lens, screen, glazing for the motor vehicle or construction industry, mirror) comprising, at its surface, an antifogging coating precursor coating. Such a substrate is more particularly described in the international application WO 2011/080 472.

METHODS OF MANUFACTURE OF THE PARTICLES

Figure 1A:
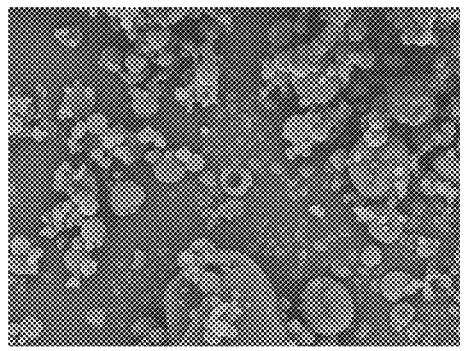
FIG. 1A, 1B SEM and optical photographs of the microspheres obtained in A2 Test 1.
Figure 1B:
Figure 1C:
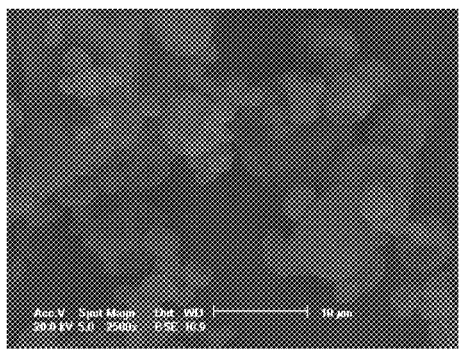
FIG. 1C, 1D SEM and optical photographs of the microspheres obtained in A3 Test 2.
Figure 1D:
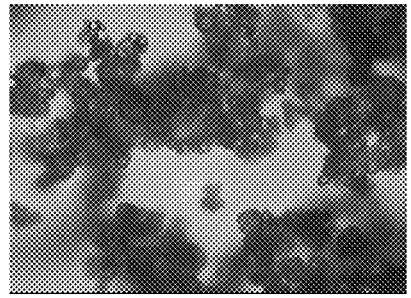
Figure 1E:
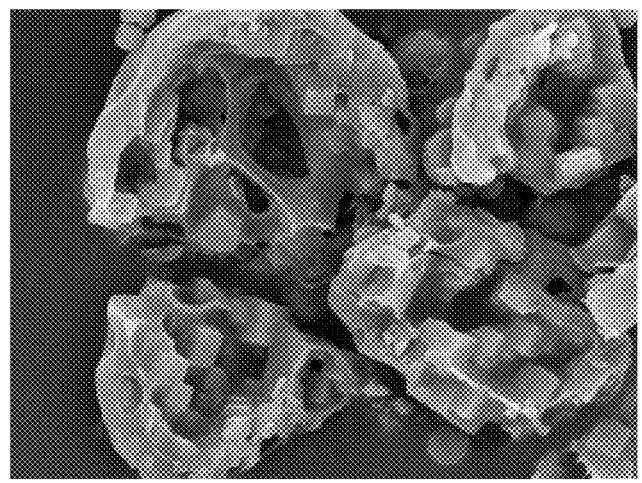
FIG. 1E SEM and optical photograph A4 Test 3.
Figure 1F:
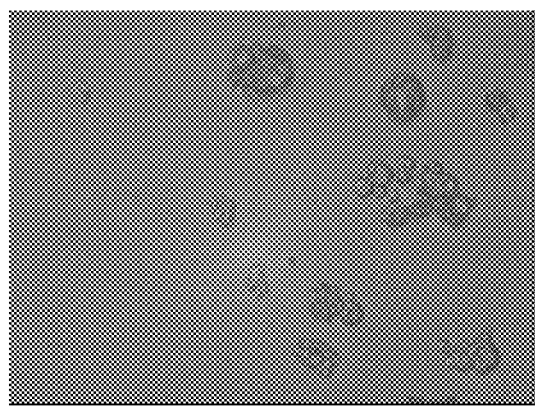
FIG. 1F optical microscopy A5 Test 4.
Figure 2:
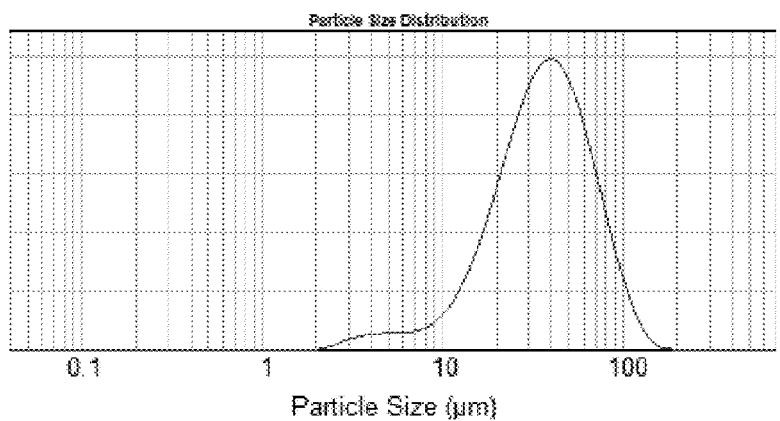
FIG. 2 is a particle size distribution curve of the microspheres of A5 Test 4.

Generally, in the present invention, the particles are obtained according to the following methods:

(A) Encapsulation by phase separation (microspheres)
  (i)—forming an aqueous mixture of a matrix material, which is preferably insoluble in water, and of at least one active agent having a solubility in water of 0.1% to 60% by weight, preferably of 0.1% to 30% by weight; and
  (ii)—forming fine droplets of the emulsion by atomization in order to obtain microspheres, the formulation of the emulsion being optimized by means of a ternary diagram model which takes into account the solubilities in water of the different constituents so that, during the evaporation of the water during the atomization, a phase separation takes place within the droplets, resulting in the appearance of a matrix-rich phase at their periphery.

(B) Encapsulation by polycondensation (microcapsules)
  i)—forming an emulsion from an oily phase containing at least one active agent having a solubility in water of 0.1% to 60% by weight, preferably of 0.1% to 30% by weight, and from an aqueous phase containing monomers capable of being condensed, and
  (ii)—carrying out the polycondensation of the monomers in order to form a membrane defining a microcapsule, the active agent having a measurable partition coefficient between the oily phase and the aqueous phase.

The partition coefficient is defined as being the ratio of the concentration of the active agent in the oily phase to the concentration of the active agent in the aqueous phase.

Preferably, the partition coefficient is greater than or equal to 1, better still greater than or equal to 1.5 and better still greater than or equal to 2.

(C) Encapsulation by modification of the Creaspher® process (patent FR 2 995 222) (microspheres)
  (i)—forming an oily phase of a water-insoluble wax, which is solid at ambient temperature, containing at least one active agent having a solubility in water of 0.1% to 60% by weight, preferably of 0.1% to 30% by weight, by heating the wax above its melting point,
  (ii)—forming a primary aqueous phase containing at least one surfactant and optionally a protective colloid, this primary aqueous phase being heated to a temperature similar to that of the oily phase,
  (iii)—forming a primary oil-in-water emulsion from the preceding phases,
  (iv)—forming a secondary aqueous phase containing a surfactant and optionally a protective colloid, this secondary aqueous phase also containing the active agent at a concentration which limits the extraction of the active agent present in the primary emulsion toward the secondary aqueous phase, preferably at a concentration close to saturation,
  (v)—adding the hot primary emulsion dropwise to the cold secondary aqueous phase in order to form, by solidification, wax droplets (microspheres) containing the active agent; and (D) Encapsulation on preformed particles (microcapsules)
  (i)—forming a particle according to the invention by one of the methods (A), (B) or (C),
  (ii)—forming a dispersion of the particles in an aqueous phase containing a water-soluble polymer,
  (iii)—rendering the initially water-soluble polymer insoluble in order to form polymer condensates which migrate to the interface of the particles, and
  (iv)—treating the polymer condensates thermally or chemically in order to form a casing on the particles (forming microcapsules).

The technology by phase separation, method (A), is known in its general principle.

However, as a result of the difference in solubility in water of the constituents of the starting formulation, the least soluble constituent will form solid particles or insoluble domains before the constituent exhibiting a greater solubility. The order of appearance and the amplitude of these phase separations will have an impact on the structure of the final microspheres. As the active agent of the invention is partially soluble in water, in order to be able to keep the agent at the core of the microsphere, it is necessary to determine the formulation of the initial preparation (solution or emulsion) so that, in the process of formation of the microspheres, the active agent does not precipitate before the constituent material of the matrix. In order to do this, according to the invention, the formulation of the emulsion is optimized by referring to a ternary diagram which takes into account the solubilities in water of the different constituents. This diagram makes it possible to define, for a desired final composition of the microcapsules, the composition ranges accessible for the initial formulations.

The first case is the case where a person skilled in the art has access to the empirical ternary diagram of the water/agent/matrix system at the given operating temperature (atomization temperature), that is to say that he has available a diagram which describes, for each given composition of the water/matrix/agent system, the number and the type of phases present at thermodynamic equilibrium.

Data present on the empirical phase diagram can be:

presence of a homogeneous liquid phase in which the agent and the matrix are soluble or coexistence of two phases, one liquid, containing x % of dissolved agent and y % of dissolved matrix, and the other solid, consisting of pure matrix or coexistence of 3 phases, one liquid, containing water and x % of agent, another solid, consisting of pure matrix, and a third liquid, consisting of pure agent.

In this case,

1/ A person skilled in the art determines the final composition of the microspheres which is desired once all the water has evaporated, that is to say the agent/matrix ratio (or the desired composition range).

2/ For these final compositions, a person skilled in the art determines, from the ternary diagram, the compositions of corresponding formulations (zones on the diagram) containing the 3 constituents, water/agent/matrix, which correspond to the agent/matrix ratio (or to the range) set.

3/ For these compositions of initial formulations, a person skilled in the art observes the phase separations liable to take place during the evaporation of the water. For this, it is sufficient to plot a straight line starting from the initial composition point toward the final composition point where all the water has evaporated and to observe the different phases and phase separations encountered.

In a typical case, the system is homogeneous (a single liquid phase) at the starting point (composition of the initial formulation) and then, when a percentage % of the water present has been removed, a phase separation takes place between a liquid phase containing water and agent and a solid phase consisting of pure matrix. When the amount of water decreases further, the coexistence of these two phases with an enriching of the liquid phase in agent is observed. Finally, when all the water has evaporated, the presence of two solid phases, respectively of pure agent and of pure matrix, is observed.

During the atomization process, the droplets exhibit a water concentration gradient. In the above case, the phase separation involving the appearance of a pure matrix phase takes place before that involving the appearance of a pure agent phase; it can therefore be predicted that the microspheres thus formed will preferably have matrix at the periphery and agent at the core.

4/ A person skilled in the art can thus, in view of the above information, prepare initial formulations such that, during evaporation, the phase separations involving the formation of matrix-rich phases take place before those involving the formation of agent-rich phases and can confirm, by tests, the structure of the microspheres.

Kinetic parameters, such as the input and output temperatures, can have an impact on the structures of the microspheres.

In the second case, where a person skilled in the art does not have available the theoretical ternary diagram, he will have to determine himself, by experimentation, by the cloud point method, for example, the zones of existences and of coexistences of the different liquid and/or solid phases of the three constituents, this indicating to him in the end the zones of phase separation.

Preferably, in the atomization method (A), use will be made of matrices which are insoluble or only slightly soluble in water, such as cellulose acetate phthalate or ethylcellulose.

The size of the microspheres obtained generally varies from 1 to 30 μm.

According to the material of the matrix, the atomization takes place at temperatures greater than the glass transition temperature of the material of the matrix, for example ethylcellulose.

The fact that the matrix is insoluble in water contributes resistance to washing by limiting the erosion of the microspheres.

The method (B) of encapsulation by polycondensation, which relates to the preparation of microcapsules, is also known in its most general aspect, in particular for encapsulation by means of silicones. Such a method is described in particular in the patent EP 2 080 552.

Typically, in this method, an emulsion is formed from an oily phase containing the active agent and from an aqueous phase containing polycondensable monomers (in particular monomers for the formation of polysiloxanes). During the process, the monomers migrate to the interface of the droplets (as a result of the pH or of the ionic strength) and their polycondensation is initiated by modifying the pH or the temperature in order to form the membrane of the microcapsules which traps the oily phase containing the active agent.

According to the invention, this method is modified by the choice of the oily phase, in particular a fluorinated oil, which is chosen so that the agent exhibits a high partition coefficient between the oily phase and the aqueous phase (and thus that the concentration of agent in the aqueous phase at equilibrium is minimal). As indicated above, the partition coefficient is defined as being the ratio of the concentration of the agent in the oily phase to the concentration of the agent in the aqueous phase. Preferably, the partition coefficient is greater than or equal to 1, better still greater than or equal to 1.5 and better still greater than or equal to 2 (measured at 25° C.).

By way of example, for the preparation of antifogging capsules, the active agent can be Zonyl® FSO100 and the fluorinated oil can be the oil HFE 7300.

Apart from the fact that the microcapsules obtained contain the active agent at their core, they have the advantage of making possible easy release of the active agent and of having a high resistance to the temperature, of the order of 120° C.

The method (C) is a modification of the process by encapsulation by the Creaspher® process relating to the preparation of microspheres which is described in particular in the patent FR 2 995 222.

The problem associated with this technology lies in the fact that, as soon as the active agent of the primary aqueous phase is partially soluble in water, there exists a high risk of the active agent being extracted from the primary aqueous phase to pass into the secondary phase before the solidification has taken place.

According to the process of the invention, the following stages are carried out:

(i) forming an oily phase of a water-insoluble wax containing at least one active agent having a solubility in water of 0.1% to 60% by weight, preferably of 0.1% to 30% by weight, by heating the wax above its melting point;

(ii) forming a primary aqueous phase containing at least one surfactant and optionally a protective colloid, this primary aqueous phase being heated to a temperature similar to that of the oily phase;

(iii) forming a primary oil-in-water emulsion from the preceding phases;

(iv) forming a secondary aqueous phase containing a surfactant and optionally a protective colloid, this secondary aqueous phase also containing the active agent at a concentration which limits the extraction of the active agent present in the primary emulsion toward the secondary aqueous phase, preferably at a concentration close to saturation with active agent and better still at a concentration corresponding to saturation with active agent at the temperature of implementation of the process;

(v) adding the hot primary emulsion to the cold secondary aqueous phase in order to form, by solidification, wax droplets (microspheres) containing the active agent.

A concentration close to saturation with active agent is understood to mean a concentration corresponding to the concentration of saturation with active agent +/−10% maximum of the saturation value.

The temperature required by the secondary aqueous phase for the implementation of the process preferably varies from 15 to 35° C.

The waxes of the oily phase are insoluble in water and generally have a melting point of greater than 35° C., preferably from 50° C. to 75° C.

Waxes which can be used are described in the patent application FR 2 995 222.

The surface-active agents used in the primary and secondary aqueous phases are generally chosen from those mentioned above.

The object of the protective colloids is to prevent the coalescence of the droplets and they are generally chosen from gum arabic, gelatin, cellulose derivatives, polyvinylpyrrolidones or polyvinyl alcohols.

The microspheres obtained by this method generally have a size of the order of 0.5 to 50 µm.

The method (D) of encapsulation is known in its general aspect and is described in particular in the patent EP 1 533 415. According to one embodiment, the method (D) is implemented and the casing of the particles is a melamine-formaldehyde polymer.

However, the method (D) cannot be applied directly to the formation of microcapsules containing a partially water-soluble active agent. Thus, according to the invention, this method is carried out starting from water-insoluble particles containing an active agent as defined.

The particles are dispersed in an aqueous phase containing an initially water-soluble polymer. The polymer is subsequently rendered insoluble, for example by modifying the pH or adding salts. Small solid polymer particles (condensates) are then formed, which particles migrate to the interface of the droplets and subsequently form, under the action of a heat or chemical treatment, a membrane over the particles.

This technology is particularly suitable for conferring, on the particles of the invention, a casing capable of being grafted by a covalent bond to the support.

The process (D) is described more specifically but non-limiting below.

The process (D) comprises the following stage or preferably consists in again encapsulating microcapsules obtained using the processes (A), (B) or (C) in a membrane.

The new microcapsules can subsequently be attached to fibers (via a binder, for example), can be released by rubbing actions and can exhibit a resistance to washing operations.

The main stages of the process are as follows:

Preparation of an aqueous solution containing a water-soluble polymer (or prepolymer). The polymer can be chosen from the products, the solubility of which can be controlled by the pH. The products can be chosen from aminoplast resins, such as urea-formaldehyde resins and melamine-formaldehyde resins, or copolymers of acrylic acid and methyl methacrylate (such as the Eudragit® poly(methacrylic acid-co-methyl methacrylate) 1:2 range), such as Eudragit® L100;

Mixing the polymer solution with the microcapsules to be coated;

Modifying the solubility of the polymer by lowering the pH.

For the aminoplast resins, the pH can be adjusted within the range from 3.5 to 4.5, preferably within the range from 3.7 to 4.2, typically 4, by addition of formic acid, for example. The desolvation of the polymer brings about the formation of condensates.

For the Eudragit® copolymers of acrylic acid and methyl methacrylate, the pH can be lowered to 5 or less by addition of a strong acid, such as PTSA (para-toluene-sulfonic acid) or by a weak acid, such as acetic acid; Typically, Eudragit® L100 is soluble for pH values above 5.5 and insoluble below;

Migration of the condensates to the water/microcapsules interface, making possible the formation of a polymer membrane around the microcapsules in order to form novel microcapsules.

Curing the membrane by increasing the temperature above the crosslinking temperature for aminoplast resins or by increasing the temperature above the temperature which makes possible the formation of a polymer film around the microcapsules.

In the case of aminoplast membranes, the microcapsules can be applied to the textile via known textile processes and chemically attached (by covalent bonds or via a binder). In the case of Eudragit® L100 membranes, the microcapsules can be applied to the textile from the known processes of the textile industry, generally at a pH of less than or equal to 5.

The invention also relates to the use of a support as presented above for conferring or reactivating a functional group on a surface of a substrate, in which the support is applied to the substrate under the effect of an external stress in order to release the active agent(s).

The external stress can be, without limitation, a mechanical, thermal or chemical stress.

In one embodiment, the substrate is an ophthalmic lens, such as a spectacle lens.

In another embodiment, the substrate is human or animal skin. In this case, the use of the support can in particular be a therapeutic (for example dermatological), cosmetic, cosmetic and nontherapeutic or nontherapeutic use, according to the nature of the active agent or agents.

The invention is illustrated in a nonlimiting way by the following examples.

EXAMPLES

Equipment and Methods

The particles obtained were characterized visually by optical and electron microscopy
optical microscope
scanning electron microscope The size distribution of the water-insoluble particles was measured with a Malvern Mastersizer 2000 laser particle size analyser.

The atomization is carried out on an SD1 tower equipped with a cocurrent internal mixing nozzle, supplied by TechniProcess.

The D1 pilot plant is a tower for drying by atomization which was designed to have an evaporative capacity of between 1 and 3 kg/h and a drying air flow rate in the vicinity of 100 kg/h.

A. Description of the Tests of Encapsulation by Phase Separation Carried Out (Microspheres)

1. Procedure for Carrying Out the Tests

Preparation of the solution to be atomized containing: the matrix, the active agent to be encapsulated and the additives, if necessary, in an aqueous medium.

Atomization of the solution on a drying tower and recovery of the particles in the powder form.

2. Test 1: Ethyl Butylacetylaminopropionate/Acacia Gum:

Formulation at pH 2 and at 50° C.:

500 g of solution, the formulation of which is favorable to the encapsulation by phase separation for placing the active agent at the center of the capsules:

| Designation | Content |
| --- | --- |
| Acacia gum | 24% |
| Ethyl butylacetylaminopropionate | 8% |
| para-Toluenesulfonic acid (PTSA) | 4% |
| Water | 64% |

Estimated content of active agent in the powder 25% [8/(24+8)]

NB: The addition of PTSA makes it possible to increase the solubility of the ethyl butylacetylaminopropionate.

Spraying Parameters:

Inlet temperature 180° C.

Outlet temperature 85-90° C.

Nozzle pressure 2 bar

3. Test 2: Xylitol/Acacia Gum:

Formulation at ambient temperature and neutral pH:

500 g of solution, the formulation of which is favorable to the encapsulation by phase separation for placing the active agent at the center of the capsules Xylitol has a solubility in water at 25° C. of 30% by weight.

| Designation | Content |
| --- | --- |
| Acacia gum | 21% |
| Xylitol | 9% |
| Water | 70% |

Estimated content of active agent in the powder 30%

Atomization Parameters:

Inlet temperature 180° C.

Outlet temperature 85.5° C.

Pressure of the nozzle 3 bar

Grayish powder (ground acacia), normal appearance of ground acacia, acacia odor, no water uptake 4. Test 3: NaCl/Acacia Gum Formulation at ambient temperature and neutral pH:

500 g of solution, the formulation of which is favorable to the encapsulation by phase separation for placing the active agent at the center of the capsules

| Designation | Content |
| --- | --- |
| Acacia gum | 21% |
| NaCl | 9% |
| Water | 70% |

Estimated content of active agent in the powder 30%

NaCl has a solubility in water of 26% by weight at 25° C.

Atomization Conditions:

Inlet temperature 180° C.

Outlet temperature 80° C.

Pressure of the nozzle 3 bar

As the crystal structure of the salt is cubic, the 3E photograph makes it possible to observe that the salt crystals are located inside the capsule (desired location).

5. Test 4: Zonyl FSO100/Ethylcellulose SD_1023.066

Formulation under cold conditions and neutral pH 300 g of solution favorable to the encapsulation by phase separation for placing the active agent at the center of the capsules.

Ethylcellulose commercially available as a 30% suspension in water (Aquacoat ECD)

| Designation | Content |
| --- | --- |
| Aquacoat ECD as suspension (30% solids content) | 50% (15% dry) |
| Zonyl | 9% |
| Triacetin | 3% |
| Water | q.s. for 100% |

Estimated content of active agent in the powder 33%

Atomization Conditions:

Inlet temperature 180° C.

Outlet temperature 80° C.

Pressure of the nozzle 3 bar

B. Description of the Encapsulation of IR3535 by the Adapted Creaspher Process (Microspheres)

1. Procedure

The slurry of microspheres is prepared in the following way:

1. Preparation of the fatty phase containing the wax and the active principle to be encapsulated, at 10° C. above the melting point of the wax used 2. Preparation of the aqueous phase 1 containing a surfactant, a protective colloid, such as acacia gum, and heating to the same temperature as the fatty phase 3. Addition of the molten fatty phase to the aqueous phase 1 and preparation of an emulsion for 10 minutes with stirring (IKA deflocculating paddle, 1200 rev/min)

4. Preparation of the aqueous phase 2 containing a surfactant and a protective colloid, such as acacia gum, cooling of the solution to 4° C.

5. Dropwise transfer of the first emulsion into the second aqueous phase with stirring (mixing paddle, 1000 rev/min)

The particles are recovered in suspension in water.

Figure 3:
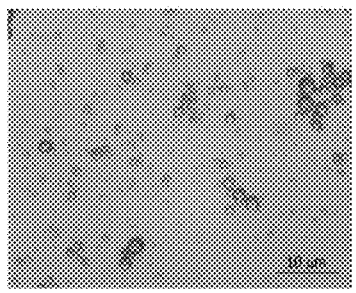
FIG. 3 optical microscopy observation B Test 1 (IR3535 in Dynasan 118)
Figure 4:
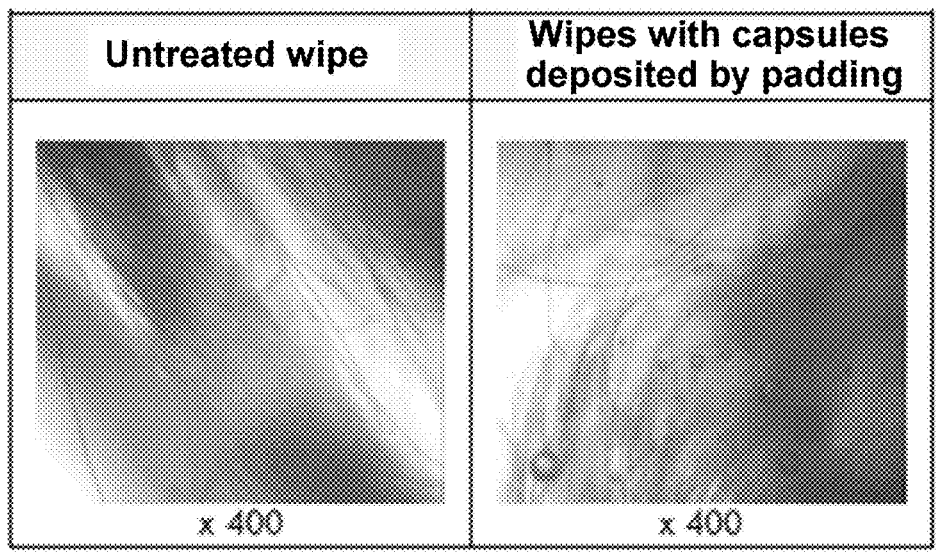
FIG. 4 optical photograph of an untreated wipe and of a wipe impregnated with microspheres.
Figure 5:
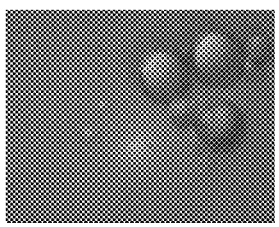
FIG. 5 an optical photograph of the microcapsules of C2 Test 1.

Test 1: Ethyl Butylacetylaminopropionate (IR3535) in Dynasan 118 (FIG. 3)

| Phase | Products/Stages | W (g) |
| --- | --- | --- |
| Fatty phase | Oil: Dynasan 118 | 84.00 |
| | Cosmetic wax. Melting point 70-74° C. | |
| | Active agent: Ethyl butylacetylaminopropionate | 56.00 |

-continued

| Phase | Products/Stages | W (g) |
|---|---|---|
| Aqueous phase 1 | Water | 129.2 |
| | Brij 721P | 0.72 |
| | Fibregum Bio | 10.08 |
| Aqueous phase 2 | Water | 103.56 |
| | Ethyl butylacetylaminopropionate | 7.2 |
| | Fibregum Bio | 8.64 |
| | Brij 721P | 0.60 |

IR3535 has a solubility in water at 20° C. of approximately 7% by weight.

Beyond, two phases are observed: an aqueous phase containing 7% of IR3535 and a liquid phase of IR3535 alone.

The particles obtained have the following characteristics:

| | |
|---|---|
| Particle size determination | 12.6 μm |
| Concentration of encapsulated active agent (estimated) | 12.6% in the slurry |
| | 37% in the dry slurry |
| | 40% in the capsule |
| Theoretical solids content | 41.8% |

Application: Deposition of the Capsules by Padding on CEMOI Textile

The bath for impregnating the wipes is composed of ethyl butylacetylaminopropionate/Dynasan 118 microspheres prepared in the preceding example and diluted in water, the concentration of microspheres in the bath being 24.5%. The padding parameters (concentration of the bath and adjustments of the apparatus) are defined in order to optimize the amount deposited as a function of the level of residue.

Calculation of the level of residue $$(\text{in } \%): \frac{(\text{weight}_{textile+deposit} - \text{weight}_{textile})}{\text{weight}_{textile}} \times 100$$

After having defined the level of residue of the textile, the concentration of microspheres in the bath is adjusted so as to deposit a predetermined amount of microspheres on the textile.

The padding parameters thus chosen make possible a deposit of microspheres of 15 μm, while keeping them intact (spherical shape), equivalent to approximately 130 mg of active agent per wipe.

The wipes are dried flat and at ambient temperature in order to limit the evaporation of the active agent related to drying in an oven.

C. Description of the Encapsulation by Polycondensation (Microcapsules)

1. Procedure
   1. Production of an acidic aqueous phase containing a cationic surfactant and stabilizers
   2. Preparation of the fatty phase containing the dissolved active agent
   In order to prevent the amphiphilic active principle from migrating into the aqueous phase during the preparation of the emulsion, it is dissolved in a solvent such that the partition coefficient of the active compound in the aqueous phase is as low as possible.
   3. Preparation of an oil-in-water emulsion
   4. Addition of the silane monomers to the emulsion. Stationary phase of two hours during which the acid hydrolysis of the silanes to give silanols and the migration of the monomers to the interface of the emulsion take place.
   5. Increase in the pH by addition of a base and formation of the membrane by a polycondensation reaction of the silanols located at the interface.
   6. Neutralization of the medium
   The particles are recovered in the slurry form.

2. Test 1: Zonyl FSO100 in Silicone

| Phases | Products | W (g) |
|---|---|---|
| Acidic aqueous phase | Water | 53.02 |
| | Tylose H15YG4 hydroxyethylcellulose | 0.57 |
| | CMC 7LC carboxymethylcellulose | 0.12 |
| | Cationic surfactant: Crodacel QM | 1.13 |
| | Volpo L3 Special | 0.38 |
| | Acetic acid | 3.79 |
| | Formic acid | 1.13 |
| Fatty phase | Active agent: Zonyl FSO 100 | 3.89 |
| | Solvent: HFE 7300 | 34.91 |
| Silicone membrane | Dynasylan A | 7.91 |
| | Dynasylan MTES | 7.91 |
| Basic medium for polycondensation | NaOH | 8.99 (q.s. for pH 5.5) |
| | NaOH | amount sufficient for pH 7.5 |
| Antimicrobial | Symdiol 68T | 1.25 |

Role of the Tylose and CMC: Rheology Modifiers

The particles obtained have the following characteristics:

| | |
|---|---|
| Particle size determination: | 8.38 μm |
| Estimated content of active agent: | 33.1% |
| Solids content (65° C.): | 18.3% |
| pH: | 7.75 |

D. Description of the Encapsulation by Melamine Around Preformed Capsules (Microcapsules)

1. Dissolution of the water-soluble polymer (melamine) with a surfactant at 35° C.
2. Mixing the polymer solution with the washed and dried capsules to be coated
3. Addition of formic acid: the polymer reacts with the formaldehyde and condenses at the surface of the capsules to begin to form the membrane
4. Increase in the temperature to 80° C. (1° C./min over 45 min): the membrane becomes rigid
5. Addition of melamine and formic acid (continuously over 90 min), crosslinking of the wall and neutralization of the excess formaldehyde. During this stage, the pH has to be kept below 4.5
6. Cooling and increase in the pH with a diethanolamine solution (the addition of DEA makes it possible to consume the residual formaldehyde).
7. The capsules are recovered in the slurry form.

The invention claimed is:

1. A process for the manufacture of a particle provided in the form of:
   a) a microcapsule comprising a solid casing including a fluid or solid phase in which at least one active agent is present; or
   b) a microsphere comprising a solid matrix in which at least one active agent is present; said active agent having a solubility in water of 0.1% to 60% by weight, wherein the process comprises the steps of:

(A)(i) forming an emulsion from an oily phase comprising fluorinated oil and containing at least one active agent having a solubility in water of 0.1% to 60% by weight, and from an aqueous phase containing silane monomers capable of being condensed for the formation of polysiloxanes; and (ii) forming a membrane defining a microcapsule by polycondensation of the silane monomers by modifying the pH or the temperature, the oily phase comprising a fluorinated oil being chosen so that the active agent exhibits a high partition coefficient between this oily phase and the aqueous phase, the partition coefficient being defined as the ratio of the concentration of the active agent in the oily phase to the concentration of the active agent in the aqueous phase; and (B)(i) forming particles by the method (A);

(ii) forming a dispersion of the particles in an aqueous phase containing a water-soluble polymer;

(iii) rendering the initially water-soluble polymer insoluble in order to form polymer condensates which migrate to particle interfaces; and (iv) treating the polymer condensates thermally or chemically in order to form a casing on the particles.

2. The process of claim 1, wherein said active agent has a solubility in water of 0.1% to 30% by weight.

3. The process of claim 1, wherein the casing of the particles is a melamine-formaldehyde polymer.

4. The process of claim 1, wherein the manufactured particle is resistant to thermal degradation at a temperature of up to and including 120° C.

\* \* \* \* \*

UNITED STATES PATENT AND TRADEMARK OFFICE
CERTIFICATE OF CORRECTION

PATENT NO.         : 10,449,128 B2
APPLICATION NO.    : 15/327732
DATED              : October 22, 2019
INVENTOR(S)        : Mamonjy Cadet et al.

Page 1 of 1

It is certified that error appears in the above-identified patent and that said Letters Patent is hereby corrected as shown below:

On the Title Page

(73) Assignee:
Delete "SATISLOH" and replace with -- SATISLOH AG --.

Signed and Sealed this
Twenty-fourth Day of November, 2020

Andrei Iancu
*Director of the United States Patent and Trademark Office*